(12) United States Patent
Ogihara et al.

(10) Patent No.: US 9,439,743 B2
(45) Date of Patent: Sep. 13, 2016

(54) FLUID DELIVERY DEVICE

(71) Applicant: PRIMETECH CORPORATION, Tokyo (JP)

(72) Inventors: Ryosuke Ogihara, Chiba (JP); Susumu Kobayashi, Nagano (JP)

(73) Assignee: PRIMETECH CORPORATION, Tokyo (JP)

( * ) Notice: Subject to any disclaimer, the term of this patent is extended or adjusted under 35 U.S.C. 154(b) by 0 days.

(21) Appl. No.: 14/834,383

(22) Filed: Aug. 24, 2015

(65) Prior Publication Data

US 2015/0359616 A1     Dec. 17, 2015

Related U.S. Application Data

(63) Continuation of application No. PCT/JP2014/000664, filed on Feb. 7, 2014.

(30) Foreign Application Priority Data

Feb. 26, 2013   (JP) .................................. 2013-036363

(51) Int. Cl.
*A61M 1/00*     (2006.01)
*A61D 7/00*     (2006.01)
*A61M 5/142*    (2006.01)

(52) U.S. Cl.
CPC ............. *A61D 7/00* (2013.01); *A61M 5/14276* (2013.01); *A61M 2205/3507* (2013.01); *A61M 2205/3569* (2013.01); *A61M 2205/3584* (2013.01)

(58) Field of Classification Search
CPC ............. A61M 2205/3507; A61M 2205/3569; A61M 2205/3584; A61M 5/14276; A61M 5/16827; A61M 2205/12; A61M 5/14228; A61M 2205/128; A61M 5/1407
See application file for complete search history.

(56) References Cited

U.S. PATENT DOCUMENTS

2002/0072733 A1\* 6/2002 Flaherty ............ A61M 5/14248
                                                         604/890.1
2003/0135159 A1    7/2003 Daily et al.
(Continued)

FOREIGN PATENT DOCUMENTS

| JP | 2001-286555 A | 10/2001 |
| JP | 2008-136525 A | 6/2008  |
| JP | 2013-015060 A | 1/2013  |

OTHER PUBLICATIONS

International Preliminary Report on Patentability for International Application No. PCT/JP2014/000664, issued by the International Bureau of WIPO on Sep. 11, 2015.
Decision to Grant issued for counterpart Japanese Application 2013-036363, issued by the Japan Patent Office on Jan. 6, 2015.
International Search Report for International Patent Application No. PCT/JP2014/000664, issued by the Japan Patent Office on Apr. 22, 2014.

(Continued)

*Primary Examiner* — Rebecca E Eisenberg

(57) ABSTRACT

There is a concern that a mechanical switch could be switched OFF due to movement of a body in which the switch is embedded. If the switch is switched OFF after being embedded, it is difficult to switch the switch back ON. Provided is a fluid delivery device that is used by being embedded within a body, including a fluid delivery mechanism for discharging fluid from a reservoir that contains the fluid to outside of the reservoir; a sending and receiving section that sends and receives information relating to control of the fluid delivery mechanism to and from an external apparatus; a power supply section that supplies power to at least one of the fluid delivery device and the sending and receiving section; and a mechanical switch that is capable of changing a supply path of the power only from a cutoff state to a conductive state.

21 Claims, 10 Drawing Sheets

(56) References Cited

U.S. PATENT DOCUMENTS

2007/0128060 A1    6/2007  Miyazaki et al.
2007/0154336 A1    7/2007  Miyazaki et al.
2010/0056874 A1    3/2010  Dijksman et al.
2012/0053514 A1*   3/2012  Robinson .......... A61M 5/14276
                                                          604/65

OTHER PUBLICATIONS

Notice of First Office Action for Patent Application No. 201480010638.1, issued by the State Intellectual Property Office of the People's Republic of China (Chinese Patent Office) on May 17, 2016.

* cited by examiner

500

VARIABLE DISCHARGE MODE

ANIMAL ID A1          WEIGHT 250(g)

TIME UNIT (Hr(s))

| | DISCHARGE RATE (ul/hr) | TIME INTERVAL (Hr(s)) | STEP NO. | NUMBER OF REPETITIONS | START TIME | END TIME |
|---|---|---|---|---|---|---|
| PROGRAM 1 | 10.0 | 1.0 | - | 30 | 09/02/26 12:00 | - |
| PROGRAM 2 | 1.0 | 7.0 | 1 | - | - | - |
| PROGRAM 3 | 10.0 | 1.0 | 1 | - | - | - |
| PROGRAM 4 | 1.0 | 7.0 | 1 | - | - | - |
| PROGRAM 5 | 10.0 | 1.0 | 1 | - | - | - |
| PROGRAM 6 | 1.0 | 7.0 | 1 | - | - | 09/03/28 12:00 |
| PROGRAM 7 | 15.0 | 24.0 | 2 | 1 | 09/03/28 12:00 | 09/03/29 12:00 |
| PROGRAM 8 | 20.0 | 24.0 | 3 | 1 | 09/03/29 12:00 | 09/03/30 12:00 |
| PROGRAM 9 | 25.0 | 24.0 | 4 | 1 | 09/03/30 12:00 | 09/04/01 12:00 |

REMAINING BATTERY LIFE 108.9(Hr(s))

[<< BACK]          [INPUT]          [CANCEL]

FIG. 9

FLUID DELIVERY DEVICE

The contents of the following Japanese and PCT patent applications are incorporated herein by reference:
NO. 2013-036363 filed on Feb. 26, 2013, and
NO. PCT/JP2014/000664 filed on Feb. 7, 2014.

BACKGROUND

1. Technical Field

The present invention relates to a fluid delivery device.

2. Related Art

A conventional apparatus is known that is embedded in a body to periodically discharge a chemical solution. In particular, a chemical solution supply apparatus is known that is embedded underneath the skin of a small animal such as a rat or marmot, and supplies a chemical solution periodically to the small animal, as shown in Patent Document 1, for example. By using test animals with such an apparatus embedded in them, the efficacy of the chemical solution is ensured. Also known is an artificial pancreas apparatus that is embedded in the body of a patient to supply the patient with insulin, such as shown in Patent Document 2, for example.

Patent Document 1: Japanese Patent Application Publication No. 2007-275548

Patent Document 2: Japanese Patent Application Publication No. 2001-286555

With such apparatuses, it is possible to use a mechanical switch as the switch for switching the power supply ON and OFF. These apparatuses are embedded within the body with the mechanical switch being in the ON state, but there is a concern that the mechanical switch could be switched OFF as a result of the movement of the body in which the apparatus is embedded. If the switch is switched OFF after the apparatus is embedded in the body, it is difficult to switch the switch back ON.

SUMMARY

According to a first aspect of the present invention, provided is a fluid delivery device that is used by being embedded within a body, comprising a fluid delivery mechanism for discharging fluid from a reservoir that contains the fluid to outside of the reservoir; a sending and receiving section that sends and receives information relating to control of the fluid delivery mechanism to and from an external apparatus; a power supply section that supplies power to at least one of the fluid delivery mechanism and the sending and receiving section; and a mechanical switch that is capable of changing a supply path of the power only from a cutoff state to a conductive state.

BRIEF DESCRIPTION OF THE DRAWINGS

FIG. 9 shows an exemplary screen for changing the setting conditions in a PC.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
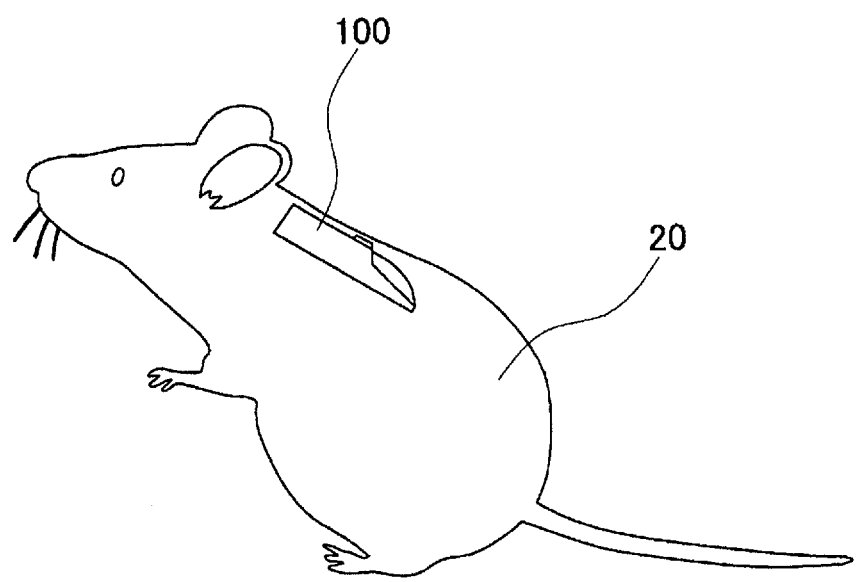
FIG. 1 shows an example of usage of a fluid delivery device 100 according to an embodiment of the present invention.

FIG. 1 shows an example of usage of a fluid delivery device 100 according to an embodiment of the present invention. As an example, the fluid delivery device 100 is used by being embedded underneath the skin near the back of a test mouse 20. The fluid delivery device 100 discharges a fluid such as a chemical solution into the body of the mouse through a micropump, according to conditions that are set in advance. The setting conditions are programmed to be conditions such as the driving start time, the driving speed, the driving time, the driving interval, and the like of the micropump, and the micropump is controlled to discharge the fluid according to the program.

The fluid is not limited to being a liquid such as a chemical solution or nutrient solution, and may be a gel or gas including a component that is to be discharged. The fluid delivery device 100 has a size that enables embedding in the test mouse 20, and therefore the embedding target is not limited to a test animal, and the fluid delivery device 100 can also be embedded in a person. By embedding the fluid delivery device 100 under the skin of a person, it is possible to periodically provide a chemical solution to the blood vessels or muscle tissue, for example.

Figure 2:
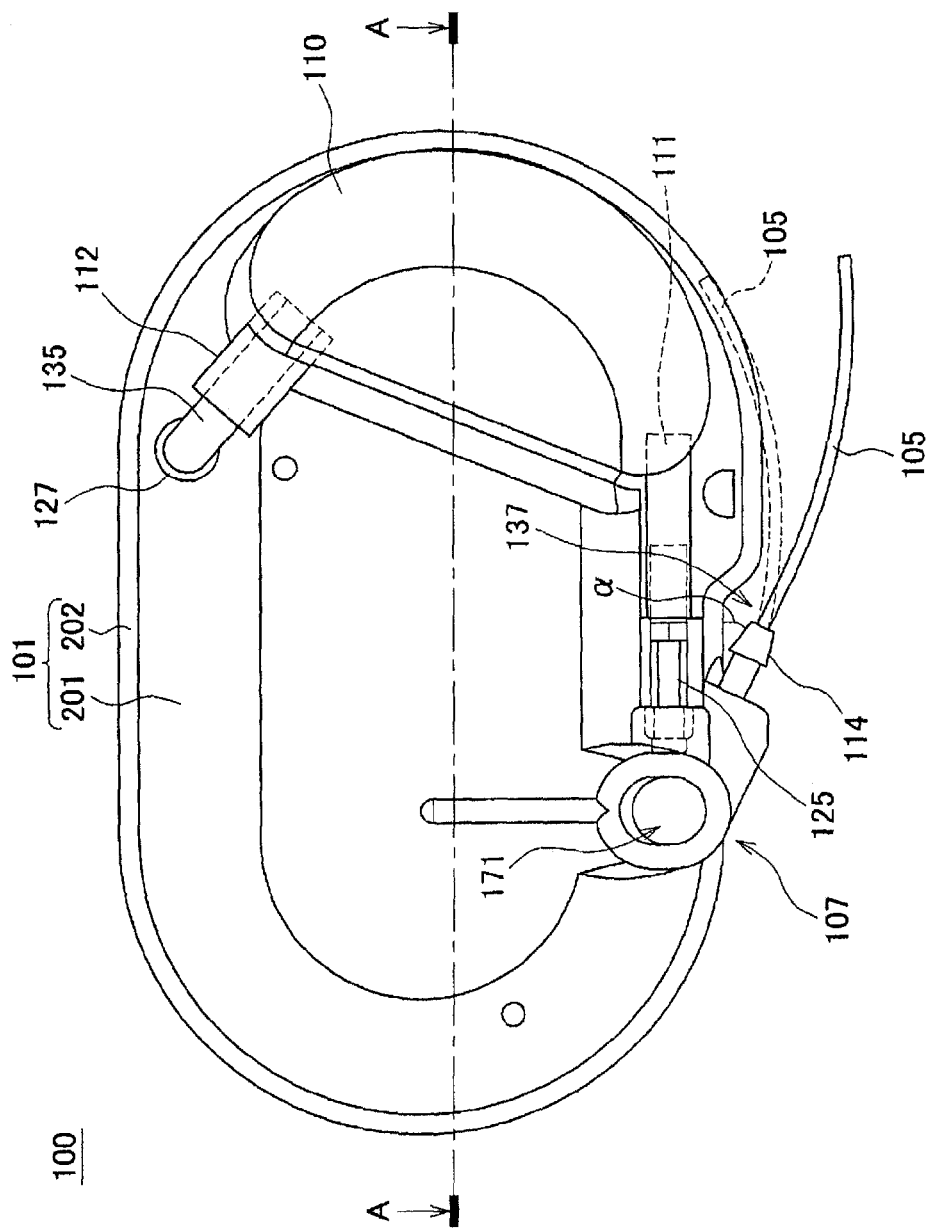
FIG. 2 is a schematic top surface view of the fluid delivery device 100.

The following described the fluid delivery device 100. FIG. 2 is a schematic top surface view of the fluid delivery device 100. The outer case 101 serving as the chassis has an overall ovular shape. The outer case 101 houses, in a sealed state, a fluid delivery mechanism that is formed from the micropump and the like, a control substrate that controls the fluid delivery mechanism, a control substrate that controls the wireless communication with the base device described further below, a wireless antenna that is used for the wireless communication, and the like. The control substrate controlling the wireless communication with the base device and the wireless antenna form a sending and receiving section. The outer case 101 blocks the ingress of bodily fluids, blood, and the like into the chassis when the fluid delivery device 100 is arranged in the body, thereby realizing stable discharge operation. Specifically, the outer case 101 includes an upper case 201 and a lower case 202 that are fused together by ultrasonic waves. The material of the outer case 101 is an acrylic resin, for example. The lower case 202 is somewhat larger than the upper case 201. Accordingly, the outer case 101 has a structure in which the outer edge portion of the lower case 202 protrudes slightly from the upper case 201 in the direction of the plane of the paper in the drawings. The outer edge portion of the lower case 202, i.e. the portion protruding from the upper case 201, functions as ribs that guide an external elastic tube 105 described further below. More specifically, when the fluid delivery device 100 is being embedded, the external elastic tube 105 is aligned with the ribs such as shown by the dashed lines in the drawing. In this way, the external elastic tube 105 is unlikely to be bent back.

The reservoir 110 is arranged on the top surface end of the outer case 101. In order to prevent the fluid delivery device 100 from becoming too large, the reservoir 110 may be directly attached to the outer case 101. In the present embodiment, the reservoir 110 is arranged on the right end in the plane of the paper of the drawing. The reservoir 110 stores a fluid such as a chemical solution. The reservoir 110 is formed as a bag that swells when filled with the fluid and contracts when the fluid is discharged. The reservoir 110 includes a fluid injection opening 111 that is used to connect to a fluid injection port 107 described further below, and a fluid ejection opening 112 that is used to connect to an internal elastic tube 135 described further below. In the present embodiment, the fluid injection opening 111 is formed in the lower left region of the reservoir 110 in the plane of the paper of the drawing, and the fluid ejection opening 112 is formed in the upper left region of the reservoir 110 in the plane of the paper of the drawing.

The fluid injection port 107 is formed on the top surface of the outer case 101. In order to prevent the fluid delivery device 100 from becoming too large, the fluid injection port 107 may be directly attached to the outer case 101. The fluid injection port 107 is arranged adjacent to the fluid injection opening 111. The fluid injection port 107 is a port that receives the fluid such as the chemical solution for filling the reservoir 110. The fluid injection port 107 is connected to the fluid injection opening 111 of the reservoir 110, via a connector 125. An aperture portion 171 is formed in the fluid injection port 107, and the aperture portion 171 has an elliptical shape.

The fluid ejection opening 112 is connected to the internal elastic tube 135. The connection between the fluid ejection opening 112 and the internal elastic tube 135 is realized through adhesion using an adhesive agent. In the present embodiment, the fluid ejection opening 112 and the internal elastic tube 135 are connected without using a connecting member such as a connector, and therefore the fluid delivery device can be expected to be smaller. The internal elastic tube 135 is routed within the outer case 101 to pass through an aperture portion 127 formed in the outer case 101 at a position adjacent to the fluid ejection opening 112. Although explained in greater detail further below, the internal elastic tube 135 routed through the inside of the outer case 101 is routed along the inner circumference of the outer case 101 and is connected to one end of a connecting section 114, which is the fluid discharge port formed adjacent to the fluid injection port 107. The external elastic tube 105 is connected to the other end of the connecting section 114. In this way, the external elastic tube 105 is connected to the outside of the connecting section 114, without the internal elastic tube 135 itself protruding to the outside. Accordingly, it is possible to attach an external elastic tube 105 with a diameter differing from the diameter of the internal elastic tube 135. In this way, the attached external elastic tube 105 can be selected as desired according to the size of the body in which the fluid delivery device is embedded.

The connecting section 114 is provided on a linear portion of the outer case 101, which has an ovular shape. When the fluid delivery device 100 is embedded in the body, there is a chance that the external elastic tube 105 will be twisted and bent back. In such a case, it is impossible to smoothly supply the chemical solution to the body in which the fluid delivery device is embedded. Therefore, in the present invention, this linear portion is provided with a concave portion 137 for housing the connecting section 114. Since the connecting section 114 is housed in the concave portion 137, a structure is realized in which it is difficult for external pressure to affect this portion. Accordingly, the connection portion between the connecting section 114 and the external elastic tube 105 is difficult to bend back. Furthermore, since the protrusion of the connecting section 114 from the outer case 101 is decreased, the burden placed on the body in which the fluid delivery device is embedded can be reduced. The connecting section 114 is provided such that the flow path of the fluid is diagonal relative to the outer circumferential surface of the outer case 101. More specifically, the connecting section 114 is provided in a state where the connecting section 114 is inclined from the inner surface that is adjacent to the bottom surface of the concave portion 137 toward the inner surface side facing this concave portion 137 and toward the opening side of the concave portion 137. The angle "β" formed by the linear portion and the connecting section 114 is preferably approximately 25 degrees.

The external elastic tube 105 is provided to follow along the outer case 101. More specifically, as described above, the connecting section 114 is arranged to be inclined relative to the linear portion, and therefore the external elastic tube 105 connected to this connecting section 114 is also inclined relative to the linear portion. The external elastic tube 105 is inherently wound in advance. As a result, the external elastic tube 105 follows along the side surface of the outer case 101 due to its own elastic force. Accordingly, the external elastic tube 105 can be embedded smoothly below the skin. Due to the configuration of the connecting section 114 and the external elastic tube 105 described above, it becomes difficult for the connection portion between the connecting section 114 and the external elastic tube 105 to be bent back, and the external elastic tube 105 can more easily follow along the ribs.

Figure 3:
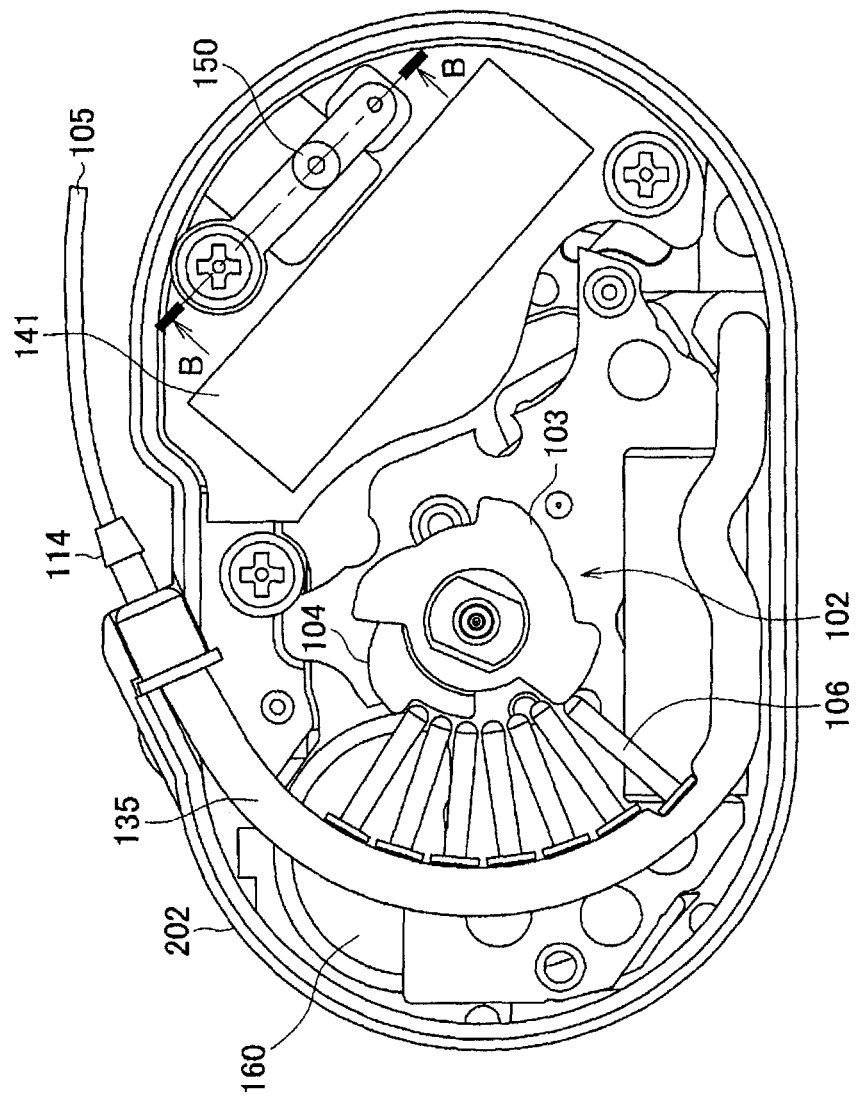
FIG. 3 is a bottom surface view of the fluid delivery device 100.

FIG. 3 is a bottom surface view of the fluid delivery device 100. The wireless antenna 141 is arranged on the back side of the reservoir 110. The wireless antenna 141 is an antenna used for wireless communication with a base device.

The mechanical switch 150 is arranged adjacent to the wireless antenna 141. The mechanical switch 150 is described in detail further below.

The micropump 102 is arranged at a position distanced from the wireless antenna 141 in the horizontal direction, which is the left-right direction in the plane of the paper of the drawing. The micropump 102 is formed from a first cam 103, a second cam 104, the internal elastic tube 135, fingers 106, and the like. The first cam 103 and the second cam 104 are fixed on the same axis, and are driven via a wheel train by a small-scale movement stepping motor with a barrel-like outer shape.

A battery 160 is arranged adjacent to the first cam 103 and the second cam 104. The battery 160 can also act as a source of noise for the wireless antenna 141, and therefore the battery 160 is arranged at a distance from the wireless antenna 141. The stepping motor and the wireless antenna 141 are driven by the same voltage that is within the voltage range of the battery 160. In other words, the stepping motor and the wireless antenna 141 are driven by the direct voltage of the battery 160. Accordingly, since the battery 160 need not include a step-up circuit or a step-down circuit, the overall size of the fluid delivery device can be decreased. There may be cases where it is desirable for the stepping motor to be provided with a larger voltage in order to increase the amount of the chemical solution supplied. In such a case, a step-up circuit may be included in the configuration.

The internal elastic tube 135 is formed from an olefin-based tube that is elastic, has excellent chemical resistance, and can strongly suppress the volatility and vaporization of moisture or the like. The internal elastic tube 135 that passes through the inside of the fluid delivery device 100 via the aperture portion 127 is arranged along the inner circumferential surface of the outer case 101 and is connected to the connecting section 114. More specifically, the internal elastic tube 135 passing through the inside of the fluid delivery device 100 is arranged horizontally along the guide groove and a portion of the internal elastic tube 135 is then arranged to follow a concentric circle whose center is the rotational center of the first cam 103 and the second cam 104 and connected to the connecting section 114. The connecting section 114 is arranged on an extension line of the internal elastic tube 135. In this way, the internal elastic tube 135 and the connecting section 114 can be arranged smoothly and continuously, and the chemical solution can be smoothly fed from the internal elastic tube 135 to the connecting section 114.

A plurality of the fingers 106 are arranged in the space adjacent to the wireless antenna 141 in the horizontal direction. The fingers 106 can also act as a source of noise for the wireless antenna 141, and therefore the fingers 106 are arranged at a distance from the wireless antenna 141. Specifically, the fingers 106 are arranged on the side of the rotational center of the cams opposite the wireless antenna 141. The fingers 106 are arranged at uniform intervals in a radial manner from the rotational center, and are arranged in finger guide grooves provided between the internal elastic tube 135 and the first cam 103 and second cam 104. In particular, each finger 106 is arranged in the horizontal direction of the outer case 101. By arranging the fingers 106 in the horizontal direction, which is a direction in which the outer case 101 has a large width, instead of in an orthogonal direction that is orthogonal to the horizontal plane that is in the horizontal direction, i.e. a direction in which the outer case 101 has a small width, it is possible to avoid an increase in the size of the outer case 101 due to the length of the fingers 106. The fingers 106 are arranged to be moveable in the radial direction within the finger guide grooves, and are pressed by the first cam 103 and the second cam 104 to close off the internal elastic tube 135.

Specifically, when the first cam 103 and the second cam 104 are rotated clockwise in FIG. 3, the cam surfaces sequentially press the fingers 106 in a clockwise order. As a result, these fingers 106 press the side surfaces of the internal elastic tube 135 from the outside to close off the internal elastic tube 135, and cause the fluid to move from the upstream side to the downstream side. When the first cam 103 and the second cam 104 are rotated further, the cam surfaces move in a direction to diverge from the fingers 106, and therefore the elastic force of the internal elastic tube 135 causes the fingers 106 to sequentially move in a direction to release the internal elastic tube 135, in the same clockwise order. By repeating this operation, the internal elastic tube 135 is repeatedly opened and closed, thereby causing peristaltic movement of the fluid from the upstream side to the downstream side such that the fluid flows toward the connecting section 114. One end of the connecting section 114 is connected to the internal elastic tube 135, and the other end is connected to the external elastic tube 105. A bio compatible olefin-based tube can be used as the external elastic tube. The bottom surface side of the outer case 101, i.e. the lower case 202, may be formed of a transparent material. In this case, the configurational components of the micropump 102 described above can be observed from the bottom surface side of the outer case 101 before the fluid delivery device is embedded in the body.

Figure 4:
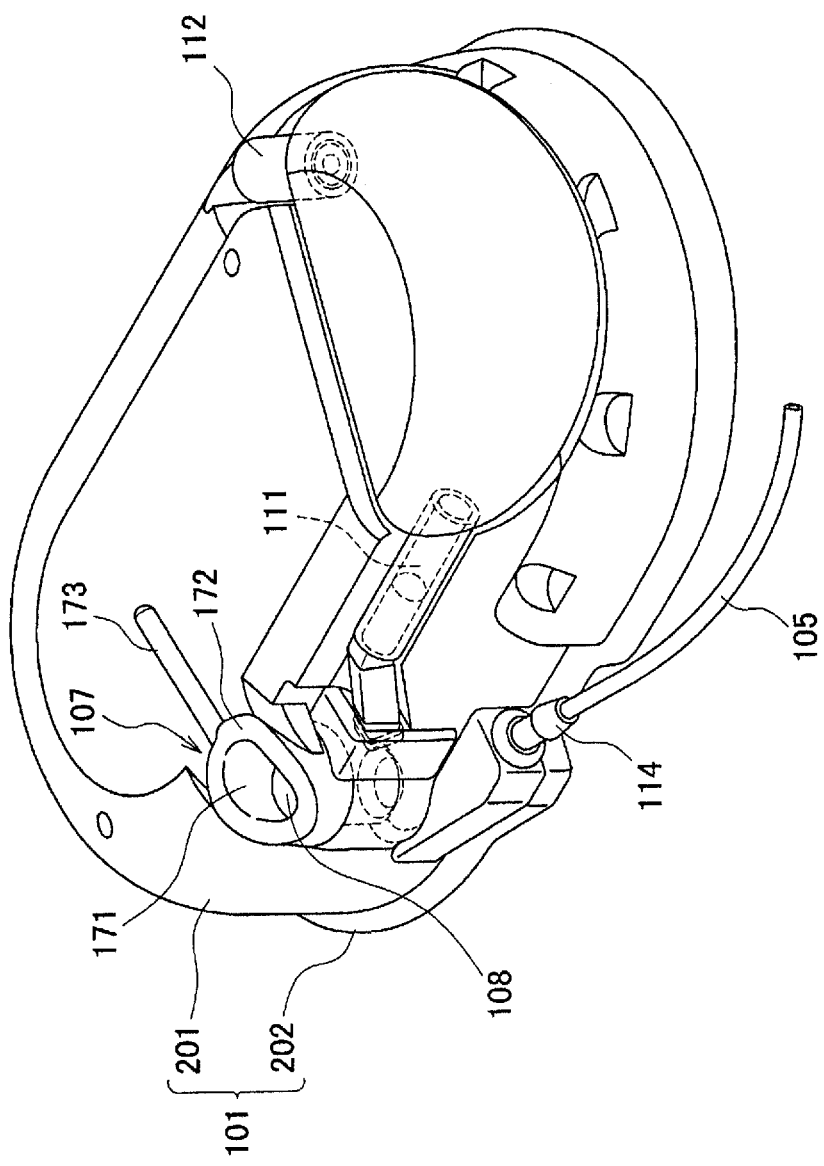
FIG. 4 is a perspective view of the fluid delivery device 100.

FIG. 4 is a perspective view of the fluid delivery device 100. As described above, the reservoir 110 and the fluid injection port 107 are arranged adjacent to each other. The fluid injection port 107 does not act a source of noise for the wireless antenna 141, and therefore the fluid injection port 107 is arranged near the reservoir 110. Although described in greater detail further below, the chemical solution is supplied to the reservoir 110 via the fluid injection port 107. The supply of this chemical solution is performed in a state where the fluid delivery device 100 is embedded in the body. In this state, the amount of the chemical solution remaining in the reservoir 110 cannot be seen by eye, and therefore the user checks the remaining amount of chemical solution within the reservoir 110 through touch, for example. Accordingly, the reservoir 110 is arranged near the top surface of the fluid delivery device 100, i.e. the surface closer to the skin, such that the reservoir 110 can be touched while the fluid delivery device 100 is embedded in the body. The fluid delivery device 100 is arranged immediately under the skin such that the top surface of the outer case 101 is on the skin surface side of the body in which the fluid delivery device 100 is embedded. Since the reservoir 110 is arranged immediately under the skin, the user can check whether fluid is stored by pressing on the reservoir 110.

The following describes the method for replenishing the fluid such as the chemical solution after the fluid delivery device 100 is embedded under the skin. A syringe is used to replenish the fluid in the reservoir 110. The needle of a syringe that is filled with the fluid to be replenished is inserted into the fluid injection stopper 108 and injects this fluid. The injected fluid is stored in the reservoir 110, via the fluid injection opening 111. The fluid injection stopper 108 is formed of an elastic material, and therefore automatically closes when the needle is removed. Accordingly, with this method for replenishing the fluid, the replenishing can be repeated a sufficient number of times.

In the manner described above, the replenishing of the fluid is performed in a state where the fluid delivery device 100 is embedded in the body, and therefore the user cannot see the fluid injection port 107 by eye. Therefore, in the present embodiment, the fluid injection port 107 protrudes slightly from the surface of the upper case 201. Accordingly, this portion creates a bump by pressing against the skin when the fluid delivery device 100 is embedded under the skin, and this bump serves as a mark of the fluid replenishment location. Accordingly, the position of the fluid injection port 107 can be recognized by the user touching the bump in the skin, for example.

On the other hand, if the fluid injection port 107 protrudes too far from the surface of the upper case 201, the chance of the fluid injection port 107 breaking the skin increases. Therefore, the fluid injection port 107 protrudes by an amount that enables a bump in the skin to be seen but does not break the skin. The protrusion amount of the fluid injection port 107 is limited in order to decrease the danger of breaking the skin in this way. The fluid injection port 107 includes a border portion 172 that is formed protruding beyond the surface of the nearby outer case 101, in a manner to border the aperture portion 171. In other words, the aperture portion 171 can be said to be formed by the border portion 172. As a result, the surface area of the skin that is pressed upward increases, and therefore it is easier for the user to see the bump in the skin. Accordingly, when touching this region, for example, it is easier to recognize the fluid injection port 107. Furthermore, a separate guide portion 173 is formed on the outer flat surface adjacent to the fluid injection port 107 to protrude beyond the nearby outer case 101, in a manner to show the position of the fluid injection port 107. Even when user cannot recognize the position of the fluid injection port 107 by the bump caused by the fluid injection port 107 alone, the user can recognize the fluid injection port 107 by sensing this guide portion 173. In the manner described above, in the present embodiment, there is a balance between the ease of recognizing the position of the fluid injection port 107 and the danger of breaking the skin.

Even when the position of the fluid injection port 107 is recognized, the fluid injection port 107 itself cannot necessarily be seen when the fluid delivery device 100 is embedded in the body. Accordingly, there are cases where the replenishing of the fluid using the syringe does not proceed smoothly. Making the fluid injection port 107 larger overall makes it easier to replenish the fluid, but also increases the size of the fluid delivery device 100. In the present embodiment, in order to expand the surface area of the fluid injection stopper 108 without increasing the size of the fluid injection port 107, the fluid injection port 107 is provided at an angle along the outer curved surface of the outer case 101. In this way, the surface area of the fluid injection stopper 108 can be increased more than in a case where the fluid injection port 107 is provided without being inclined relative to the outer case 101. Accordingly, the user can easily replenish the fluid using a syringe.

The fluid injection port 107 and the connecting section 114 are arranged along the fluid replenishment direction relative to the outer case 101, i.e. the orthogonal direction that is the up-down direction in the plane of the paper of the drawing. Furthermore, as described above, the fluid injection opening 111 is arranged adjacent to the fluid injection port 107, and the fluid ejection opening 112 is arranged at a distance from the fluid injection opening 111. In other words, the fluid injection port 107, the fluid injection opening 111, and the fluid ejection opening 112 are arranged along the outer circumference of the outer case 101. With this arrangement, the internal elastic tube 135 routed through the inside from the aperture portion 127 can be suitably arranged along the inner circumferential surface of the outer case 101 to the connecting section 114.

Figure 5:
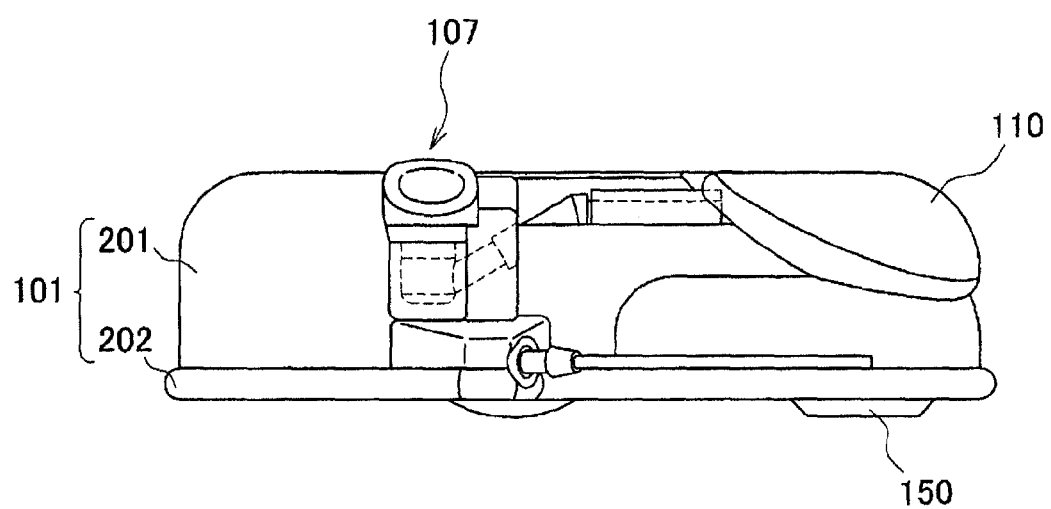
FIG. 5 is a side surface view of the fluid delivery device 100.

FIG. 5 is a side surface view of the fluid delivery device 100. As described above, the fluid injection port 107 protrudes slightly beyond the outer case 101. The mechanical switch 150 is arranged on a surface of the outer case 101 that is opposite the surface on which the reservoir 110 is arranged. The mechanical switch 150 also protrudes slightly beyond the outer case 101 in a state before the fluid delivery device 100 is embedded within the body, i.e. when the switch is in the OFF state. Although explained in greater detail further below, the mechanical switch 150 is pressed into the inside of the outer case 101 by the switch being turned ON. Furthermore, if the mechanical switch 150 is on the surface opposite the surface on which the reservoir 110 is arranged, then external force such as touching by the user is not directly applied to the mechanical switch 150. Accordingly, the chance of the mechanical switch 150 being damaged is decreased.

Figure 6:
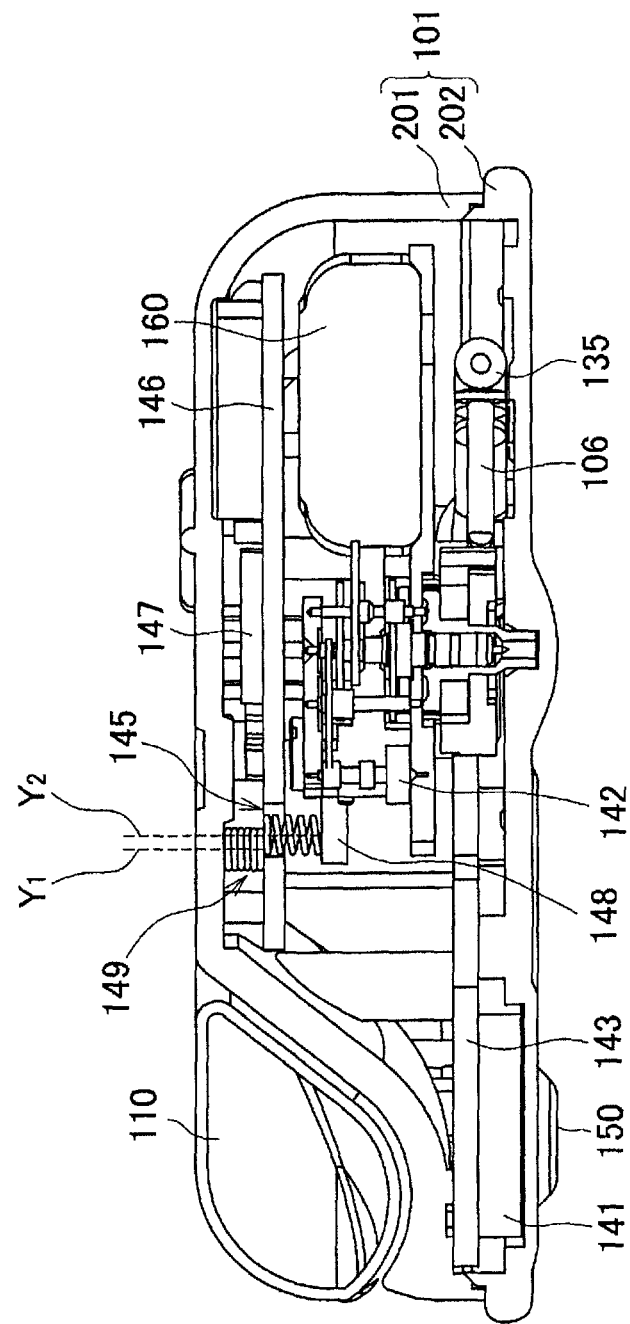
FIG. 6 is a cross-sectional view of the fluid delivery device 100 over the line A-A shown in FIG. 2.

FIG. 6 is a cross-sectional view of the fluid delivery device 100 over the line A-A shown in FIG. 2. The control substrate 143 that controls the wireless communication with the base device is arranged on the back side of the reservoir 110. The wireless antenna 141 is arranged on the lower case 202 side surface of the control substrate 143. With this arrangement, the wireless antenna 141 can be arranged far from the noise sources such as the battery 160, and therefore the effect of noise during communication can be reduced. The control substrate 146 that controls the fluid delivery mechanism is arranged at a distance to the right of the reservoir 110 in the plane of the paper of the drawing. Electronic components such as a CPU 147 for controlling the fluid delivery mechanism are arranged on the control substrate 146. An aperture portion 145 is provided in the control substrate 146. A circuit substrate 148 is provided below the aperture portion 145 of the control substrate 146. A conductive member 149 is arranged and secured between the circuit substrate 148 and the upper case 201 through the aperture portion 145. The bottom end of the conductive member 149 contacts an electrode provided on the top surface of the circuit substrate 148, and the side surface portion of the conductive member 149 positioned within the aperture portion 145 contacts an electrode provided on the left side inner wall of the aperture portion 145. In this way, the control substrate 146 and the circuit substrate 148 are electrically connected.

The conductive member 149 is preferably shaped as a coil spring. In this way, the contact pressure between the conductive member 149 and the electrode of the circuit substrate 148 can be strengthened. Furthermore, the conductive member 149 is secured in a state where the central axis Y1 of the top end is shifted to the left relative to the central axis Y2 of the bottom end. Therefore, a pulling force to the left acts on the portion of the conductive member 149 positioned within the aperture portion 145. As a result, the contact pressure on the electrode positioned on the inner wall of the aperture portion 145 is strengthened. By strengthening the contact pressure on the electrodes in this manner, instability in the electrical connection can be restricted. The stepping motor 142 and the battery 160 are arranged on a substrate below the control substrate 146. The stepping motor 142 is driven under control of the CPU 147.

In the outer case 101, the space housing the stepping motor 142 and the space above which the reservoir 110 is arranged are adjacent to each other, and the wireless antenna 141 is arranged in the space above which the reservoir 110 is arranged. By arranging the wireless antenna 141 in the space below the reservoir 110, which occupies a large amount of volume in the fluid delivery device 100, the wireless antenna 141 can be arranged far from the space in which the stepping motor 142 is arranged. Accordingly, the noise affecting the communication by the wireless antenna 141 can be decreased.

Figure 7A:
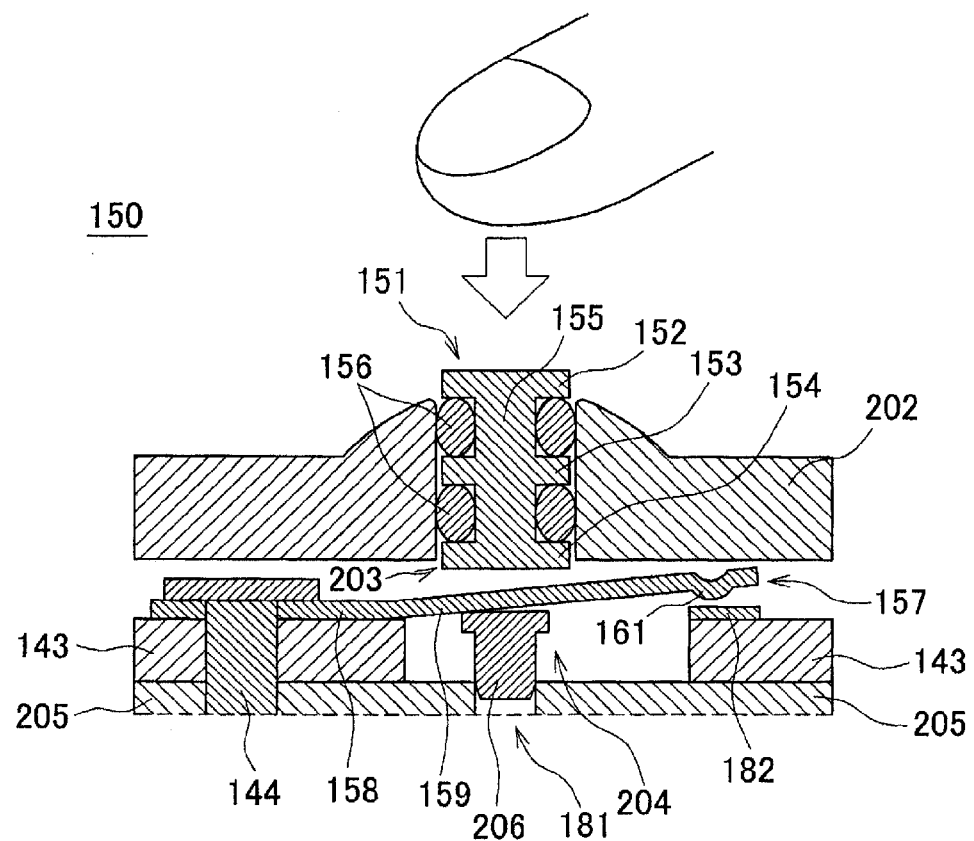
FIGS. 7A and 7B are each a cross-sectional view of the fluid delivery device 100 over the line B-B shown in FIG. 3.
Figure 7B:
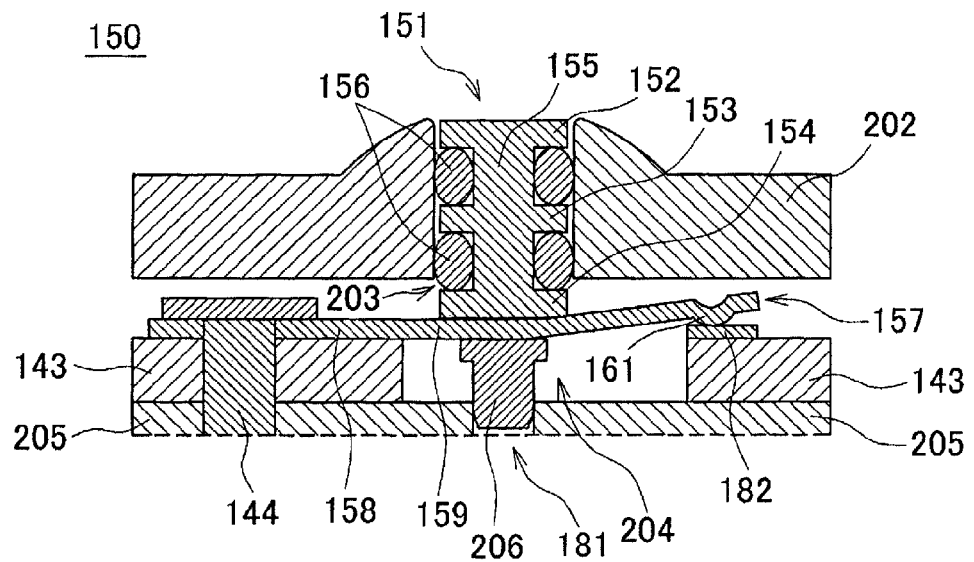

FIGS. 7A and 7B are each a cross-sectional view of the fluid delivery device 100 over the line B-B shown in FIG. 3. FIG. 7A shows a state before the mechanical switch 150 is turned ON. The mechanical switch 150 is a switch that is switched ON as a result of at least a portion of a mechanism being displaced by user manipulation. In the present embodiment, the mechanical switch 150 can only be changed from the OFF state, which is a state where the power supply path is cut off, to the ON state, which is the conductive state. In other words, the mechanical switch 150 is an irreversible switch in which the displacement is one way. The mechanical switch 150 is described using, as an example, a press switch that does not return to the OFF position after being pressed once into the ON position. The mechanical switch 150 includes a pressing section 151 and 0-rings 156.

The pressing section 151 is arranged in an aperture portion 203 provided in the lower case 202. The pressing section 151 has a three-stage structure including an upper portion 152, a middle portion 153, and a lower portion 154, which are all shaped as circular plates. The upper portion 152, the middle portion 153, and the lower portion 154 are formed with intervals therebetween. As a result, space is formed between the upper portion 152 and the middle portion 153 and space is formed between the middle portion 153 and the lower portion 154. A strut 155 is arranged to connect the central portions of the upper portion 152, the middle portion 153, and the lower portion 154. As a result, the pressing section 151 forms a two-stage ring-shaped space in the pressing direction, i.e. the orthogonal direction that is the up-down direction in the plane of the paper of the drawing. Furthermore, the upper portion 152, the middle portion 153, and the lower portion 154 have the same diameter. Since the width of the entire pressing section 151 is constant, the pressing section 151 can be inserted into the aperture portion 203 from outside the lower case 202. The pressing section 151 can be inserted after the upper case 201 and the lower case 202 are fused together, and this is beneficial from the viewpoint of the manufacturing process.

The pressing section 151 is formed of a resin material. As described above, the pressing section 151 is arranged in the aperture portion 203 provided in the lower case 202, and therefore is exposed to the outside of the lower case 202. Accordingly, the pressing section 151 is exposed to the bodily fluids of the body in which the fluid delivery device 100 is embedded. Compared to a case where metal is used as the material for the pressing section 151, using a resin material as the material of the pressing section 151 can decrease decay caused by bodily fluids and can restrict electrical conduction caused by bodily fluids.

An O-ring 156 is arranged in each of the spaces in the two-stage structure formed in the pressing section 151. In this way, by arranging the O-rings 156 at two stages in the pressing direction, it is difficult for bodily fluids to enter into the inside of the fluid delivery device 100. In order to increase the effect of restricting the penetration of bodily fluids, a ring-shaped space with three or more stages may be formed in the pressing section 151 and three or more O-rings 156 may be arranged respectively in these spaces. Obviously a ring-shaped space with only one stage may be formed in the pressing section 151 and one O-ring 156 may be arranged in this space.

The control substrate 143 is arranged opposite the lower case 202. A notched portion 204 is formed in the control substrate 143 at a position corresponding to the pressing section 151. Furthermore, an electrode 182 is formed on the control substrate 143 to electrically connect to the battery 160.

A switch spring 157 is arranged opposite the pressing section 151. More specifically, the switch spring 157 is attached to the control substrate 143 via a screw 144. The switch spring 157 is board shaped and has a linear portion 158 and a bent portion 159. Specifically, the linear portion 158 is the portion from the screw 144 side end of the switch spring 157 to the portion immediately in front of the notched portion 204, and the bent portion 159 is the portion from the position immediately in front of the notched portion 204 to the end of the switch spring 157 opposite the screw 144 side end. The linear portion 158 follows along the control substrate 143. On the other hand, the bent portion 159 is inclined relative to the surface of the control substrate 143, and does not follow the control substrate 143. In other words, the bent portion 159 extends toward the pressing section 151 side. A curved portion 161 that is curved downward in the plane of the paper of the drawing is formed on the bent portion 159 side end of the switch spring 157.

A resin member 205 is arranged on the surface of the control substrate 143 that is opposite the surface on which the switch spring 157 is arranged. A concave portion 181 is formed in the resin member 205 at a position corresponding to the pressing section 151.

A support member 206 is arranged in the concave portion 181. The support member 206 has an overall width that is slightly greater than the width of the concave portion 181. However, the bottom end of the support member 206 is formed to be slightly narrower than the concave portion 181. The support member 206 is secured in a state where the bottom end of the support member 206 is arranged within the concave portion 181 and the portion of the support member 206 with the greater width is slightly inserted into the concave portion 181. The top end of the support member 206 protrudes slightly beyond the control substrate 143. The support member 206 supports the bent portion 159. In this way, as shown in FIG. 7A, in a state before the mechanical switch 150 is turned ON, the switch spring 157 and the electrode 182 are not in contact with each other. In this state, the battery 160 is in a non-conducting state. Accordingly, the wireless antenna 141 and the stepping motor 142 are not supplied with power, and therefore the power of the battery 160 is not consumed.

As shown in FIG. 7A, in the state before the mechanical switch 150 is turned ON, the tip portion of the pressing section 151 protrudes to the outside of the lower case 202. The user can turn ON the mechanical switch 150 by pressing the tip portion such that the pressing section 151 is pressed into the inside of the lower case 202.

FIG. 7B shows a state after the mechanical switch 150 has been turned ON. When the pressing section 151 is pressed into the inside of the lower case 202, the pressing section 151 contacts the bent portion 159 of the switch spring 157 and the bent portion 159 of the switch spring 157 is pressed downward in the plane of the paper of the drawing. When this occurs, the support member 206 is pressed downward in the plane of the paper of the drawing via the bent portion 159 of the switch spring 157, to be pressed into and engaged with the concave portion 181. As a result, the support member 206 is strongly secured, and therefore the support member 206 is prevented from returning to its original position. In this way, the bent portion 159 is prevented from being lifted up by the support member 206. Furthermore, as a result of pressing down on the bent portion 159 of the switch spring 157, the curved portion 161 is pressed downward in the plane of the paper of the drawing to press against the electrode 182. As a result, the battery 160 enters a conductive state and power is supplied to the wireless antenna 141 and the stepping motor 142.

Furthermore, in the pressed state, the tip portion of the pressing section 151 is in approximately the same plane as the surface of the lower case 202. Accordingly, at the stage where the fluid delivery device 100 is embedded into the body, protruberance from the lower case 202 of the pressing section 151 is reduced. As a result, the burden placed on the body in which the fluid delivery device 100 is embedded can be reduced. When the mechanical switch 150 is pressed once, the pressed state is maintained by the frictional force acting on the contact surface between the inner wall of the aperture portion 203 and the O-rings 156.

If the mechanical switch is switched OFF after the fluid delivery device 100 is embedded in the body, it is difficult to switch the mechanical switch back ON. Furthermore, if the fluid delivery device 100 is being used for clinical testing, accurate data is desired for the clinical testing, and therefore it is important that the mechanical switch remain ON when the fluid delivery device is embedded within the body. With the present embodiment, the mechanical switch 150 can only change from OFF to ON. Accordingly, when the fluid delivery device 100 is embedded in the body while the mechanical switch 150 is in the pressed state, the possibility of the mechanical switch 150 being switched OFF due to movement of the body in which the fluid delivery device 100 is embedded can be reduced. By turning ON the mechanical switch 150 immediately prior to embedding the fluid delivery device 100 in the body, it is possible to restrict wasted power consumption, and therefore power efficiency can be expected. Furthermore, by using the mechanical switch 150, a smaller device can be realized than in a case where a Reed switch is used, for example.

In the above description, the mechanical switch 150 includes the O-rings 156 as the sealing component, but the lower case 202 may also include a sealing component. For example, along with forming the pressing section 151 as a cylinder, a sealing component may be arranged along the inner wall of the aperture portion 203 in the lower case 202 where the pressing section 151 is arranged. In this way, it is possible to prevent the penetration of bodily fluids from the gap between the pressing section 151 and the lower case 202. In this case, by arranging the sealing component along the entire inner wall of the aperture portion 203 and increasing the contact surface area between the sealing component and the pressing section 151, it becomes easy to hold the pressing section 151 in the pressed state.

In the above description, the upper portion 152, the middle portion 153, and the lower portion 154 all have the same shape, but the end of the lower portion 154 on the control substrate 143 side may have a diameter that is greater than the diameter of the aperture portion 203. With this configuration, the control substrate 143 side end of the lower portion 154 functions as a stopper that stops the pressing section 151 from returning in a direction opposite the pressing direction. In this case, the pressing section 151 can be inserted into the aperture portion 203 from the inside of the lower case 202.

In the above description, the switch spring 157 and the support member 206 are configured as separate components, but these components may be formed integrally. For example, by providing the switch spring with a through-hole and inserting the support member into this through-hole, it is possible to form an integrated structure in which the support member is a protrusion relative to the switch spring. In this case, if the protrusion is pressed into and engaged with the concave portion 181, the position of the switch spring can be secured as long as this protrusion is secured in the concave portion 181. Accordingly, even if it were assumed that the pressing force on the switch spring were to weaken due to the pressing section 151 returning in a direction opposite the pressing direction, the switch spring could still be restricted from moving away from the electrode 182.

Figure 8:
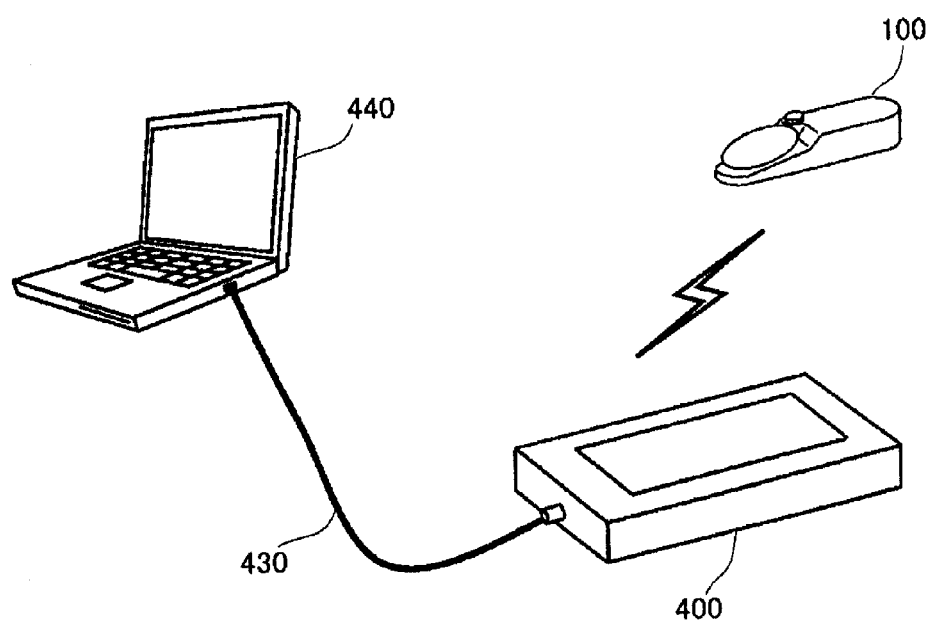
FIG. 8 is a schematic view of a communication system 300 including the fluid delivery device 100.

FIG. 8 is a schematic view of a communication system 300 including the fluid delivery device 100. The communication system 300 includes a PC 440 and a base device 400 in addition to the fluid delivery device 100. The user inputs setting conditions such as the start time for discharging the fluid, the discharge speed, the discharge amount, the discharge interval, and the number of repetitions, using software of the PC 440. The PC 440 converts the input setting conditions into a prescribed command, and transmits the command to the base device 400 via a LAN cable 430.

The base device 400 is a sending and receiving device that includes a CPU, a memory, a power supply, a sending and receiving circuit, and the like. The base device 400 receives the setting conditions transmitted from the PC 440 and transmits these setting conditions to the fluid delivery device 100 via a communication network.

The fluid delivery device 100 receives the setting conditions transmitted from the base device 400 and operates according to these setting conditions. As described above, the fluid delivery device 100 is extremely small. Therefore, a low-capacity memory is provided to store log information for each predetermined period relating to the operation. The log information can be exemplified by information in which there is an association between the supplied chemical solution amount and the time during which the chemical solution was supplied.

This log information is stored in the memory of the base device 400, which is a separate apparatus from the fluid delivery device 100. More specifically, upon supplying the chemical solution according to the setting information, the fluid delivery device 100 generates, as the log information, information in which the supplied chemical solution amount is associated with the time during which the chemical solution was supplied. The fluid delivery device 100 stores the generated log information within the fluid delivery device 100, and periodically transmits the stored log information to the base device 400.

The base device 400 receives the log information transmitted from the fluid delivery device 100, and stores the received log information in the memory. The base device 400 periodically transmits the log information to the PC 440 via the LAN cable 430.

In this way, with the communication system of the present embodiment, the communication between the base device 400 and the fluid delivery device 100 is performed wirelessly. Accordingly, even after the fluid delivery device 100 is embedded under the skin in the body, it is possible to change the setting conditions of the fluid delivery device 100 without the user extracting the fluid delivery device 100 from the body. The user can change the setting conditions dynamically according to the physical condition of the body in which the fluid delivery device 100 is embedded, for example.

If communication is not being performed between the PC 440 and the base device 400, the PC 440 and the base device 400 need not be connected by the LAN cable 430. Even if the base device 400 is not connected to the PC 440, the base device 400 can receive and store the log information transmitted from the fluid delivery device 100. In other words, the base device 400 can operate independently from the PC 440.

In the present embodiment, the wireless antenna 141 selectively switches to one of a plurality of frequency bands to send and receive the setting conditions. Accordingly, it is possible to perform wireless communication between the base device 400 and the fluid delivery device 100 by switching to a suitable frequency band according to the countries that are destinations of the fluid delivery device 100 and the base device 400, for example. Upon receiving input from the user to switch the frequency, the PC 440 transmits to the base device 400 information indicating the frequency that is to be switched to. Furthermore, the PC 440 transmits this information to the fluid delivery device 100 via the base device 400.

FIG. 9 shows an exemplary screen for changing the setting conditions in a PC. The setting condition change is performed by the user using an input device such as a keyboard to input numerical values or the like into a window

500 shown in the display of the PC 440. A plurality of types of conditions that can be set are prepared, but this description relates to a variable discharge mode that enables the discharge amount and the discharge time interval to be set as desired.

An ID is given to the animal into which the fluid delivery device 100 will be embedded, and weight information or the like that is input in advance is displayed. A time unit can be selected for the settings, e.g. units of one minute or one hour.

The items that can be set by the user include discharge rate, time interval, step number, number of repetitions, start time, and end time. In the settings shown in the drawing, first, discharge is performed continuously for 1.0 hours with a discharge rate of 10.0 μl per hour (program 1) and then discharge is performed continuously for 7.0 hours with a discharge rate of 1.0 μl per hour (program 2). After this, program 3 having the same conditions as program 1, program 4 having the same conditions as program 2, program 5 having the same conditions as program 1, and program 6 having the same conditions as program 2 are performed in the stated order. After this, a shared step number of "1" is given to these programs 1 to 6, and programs 1 to 6 are repeated 30 times according to the setting for the number of repetitions. The start time for this series is set to be 12:00 on Feb. 26, 2009. In this case, the end time is calculated and displayed dynamically. For program 7, a step number of "2" is given, and discharge is performed for 24.0 hours with a discharge rate of 15.0 μl per hour. Since the step number "2" is not given to any other programs and the number of repetitions is set to 1, the program 7 is only repeated once. The programs 8 and 9 are performed in the same manner as program 7. As shown in the drawing, the remaining battery life of the battery 160 is shown in time.

Upon receiving a setting input from the user, the PC 440 visibly displays how the fluid is provided to the animal that is the target, according to the set conditions.

Figure 10:
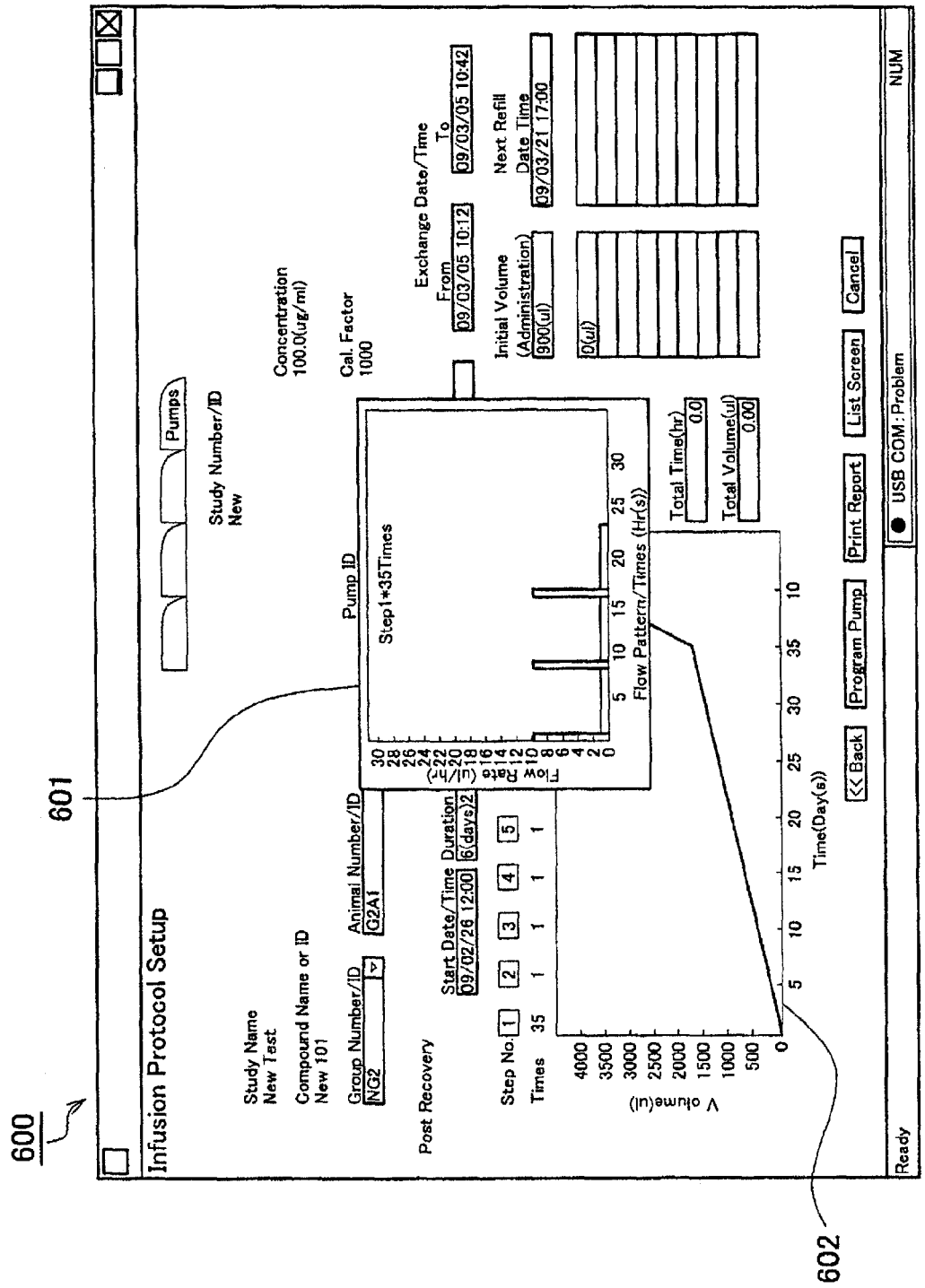
FIG. 10 shows an exemplary interface screen in the PC.

FIG. 10 shows an exemplary interface screen in the PC. When the window 500 that is the setting screen is closed, the window 600 is displayed. The discharge rate and time interval for each step number are graphed and displayed in the window 601. The cumulative discharge amount discharged into the target animal when all of the programs have been performed is graphed and shown in the window 602.

With the present system configured in this manner, it is possible to realize a repeating function for the medicinal solution providing program, particularly for a micropump that is embedded permanently in a small animal. As a result, it is possible to create a periodic rhythm for the concentration of the medical solution in the body, which is important for evaluating medicinal efficacy.

In the above description, the battery 160 supplies power to both the wireless antenna 141 and the stepping motor 142, but instead, a battery for the wireless antenna 141 and a battery for the stepping motor 142 may be provided separately. In this case, a mechanical switch may be provided in correspondence with each battery. Instead, a single mechanical switch can be provided for both the battery for the wireless antenna 141 and the battery for the stepping motor 142. In this case, the mechanical switch simultaneously touches contact points for electrodes corresponding respectively to the batteries in response to the pressing action of the user.

In the above description, a press switch is used as an example of the mechanical switch, but the mechanical switch is not limited to this. The mechanical switch may be a slide switch or a rotating switch. As an example of a slide switch, the switch can be switched from OFF to ON in response to at least a portion of a mechanism being slid by a prescribed amount. A slide switch includes a sliding member that is opposite the control substrate and slides in a relatively horizontal direction in response to user manipulation, and a metal hooked member. A wireless antenna electrode is electrically connected to the wireless antenna on the control substrate. A concave portion is formed in the control substrate at a position distanced from the wireless antenna electrode, and a battery electrode that is electrically connected to the battery is formed within the concave portion. The hooked member is configured such that, when one end thereof contacts the battery electrode by being inserted into the concave portion, the other end contacts the wireless antenna electrode. When the slide switch is OFF, the one end of the hooked member is not inserted into the concave portion, and the wireless antenna electrode and battery electrode are in a non-conductive state. When the sliding component is slid forward by the user, the hooked member slides according to the sliding of this sliding member. As a result, when the one end of the hooked member is inserted into the concave portion, the hooked member contacts the battery electrode in the concave portion and causes the wireless antenna electrode and the battery electrode to be in a conductive state. Furthermore, the hooked member is configured to be capable of sliding forward, but to be incapable of returning in an opposite direction after having once being inserted into the concave portion and passing beyond the concave portion.

As an example of a rotating switch, the switch can be switched from OFF to ON by rotating at least a portion of a mechanism by a prescribed amount. A rotating switch includes a rotating member shaped as a column that is opposite the control substrate and rotates in response to user manipulation. A metal piece that is biased in the pressing direction is arranged on the control substrate side of the rotating member. The metal piece is configured to move according to the rotation of the rotating member and, upon reaching a predetermined position, to provide conduction between the wireless antenna electrode and the battery electrode. For example, a concave portion is formed between the wireless antenna electrode and the battery electrode, and conduction between the wireless antenna electrode and the battery electrode is realized by the metal piece being inserted into the concave portion. Furthermore, the metal piece that is biased in the pressing direction cannot move past the concave portion after being inserted into the concave portion once.

The structure of the switch itself need not be mechanical. For example, the mechanical switch can be configured by combining a mechanical structure and a semiconductor sensor.

In the above description, the battery electrode and the wireless antenna electrode are physically separated from each other, and therefore absolutely no current flows while in the OFF state. However, the battery electrode and the wireless antenna electrode need not be physically separated from each other. In this case, it is possible to realize a suspended state in which a very weak current flows, but since the power consumption in the suspended state is sufficiently small relative to the power consumption in the ON state, the suspended state can be treated as the OFF state.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

LIST OF REFERENCE NUMERALS

20: test mouse, 100: fluid delivery device, 101: outer case, 102: micropump, 103: first cam, 104: second cam, 105: external elastic tube, 106: finger, 107: fluid injection port, 108: fluid injection stopper, 110: reservoir, 111: fluid injection opening, 112: fluid ejection opening, 114: connecting section, 125: connector, 127: aperture portion, 135: internal elastic tube, 137: concave portion, 141: wireless antenna, 142: stepping motor, 143: control substrate, 144: screw, 145: aperture portion, 146: control substrate, 147: CPU, 148: circuit substrate, 149: conductive member, 150: mechanical switch, 151: pressing section, 152: upper portion, 153: middle portion, 154: lower portion, 155: strut, 156: O-ring, 157: switch spring, 158: linear portion, 159: bent portion, 160: battery, 161: curved portion, 171: aperture portion, 172: border portion, 173: guide portion, 181: concave portion, 182: electrode, 201: upper case, 202: lower case, 203: aperture portion, 204: notched portion, 205: resin member, 206: support member, 300: communication system, 400: base device, 430: LAN cable, 440: PC, 500, 600, 601, 602: window

What is claimed is:

1. A fluid delivery device that is used by being embedded within a body, comprising:
    a fluid delivery mechanism for discharging fluid from a reservoir that contains the fluid to outside;
    a sending and receiving section that wirelessly sends and receives information relating to control of the fluid delivery mechanism to and from an external apparatus;
    a power supply section that supplies power to at least one of the fluid delivery mechanism and the sending and receiving section; and
    a mechanical switch that has a stationary part and a movable part whose movement is capable of changing a supply path of the power only from a cutoff state to a conductive state, the movable part remaining fixed to the fluid delivery device after being moved.

2. The fluid delivery device according to claim 1, wherein the mechanical switch is a press switch that does not return once pressed.

3. The fluid delivery device according to claim 2, wherein when in a pressed state, a tip portion of the press switch is in the same plane defined by a nearby surface of a chassis of the fluid delivery device.

4. The fluid delivery device according to claim 2, wherein the press switch is maintained in a pressed state by a force of friction of a sealing component provided between the press switch and a chassis of the fluid delivery device.

5. The fluid delivery device according to claim 4, wherein the sealing component is provided at two stages in a pressing direction of the press switch.

6. The fluid delivery device according to claim 2, wherein a pressing direction of the press switch is a direction substantially perpendicular to an outer main surface of a chassis of the fluid delivery device.

7. The fluid delivery device according to claim 1, wherein the mechanical switch is arranged on a surface of a chassis of the fluid delivery device that is different from a surface on which the reservoir is arranged.

8. The fluid delivery device according to claim 1, comprising:
    a fluid injection port that receives the fluid to be replenished in the reservoir, wherein
    the fluid injection port is provided along an outer curved surface of a chassis of the fluid delivery device, with an inclination relative to the outer curved surface.

9. The fluid delivery device according to claim 8, wherein an aperture portion in the fluid injection port has an elliptical shape.

10. The fluid delivery device according to claim 8, comprising:
    a border portion that is formed protruding from the nearby surface of the chassis in a manner to border an aperture portion of the fluid injection port.

11. The fluid delivery device according to claim 8, comprising:
    a guide portion formed protruding from the nearby surface of the chassis in a manner to indicate a position of an aperture portion of the fluid injection port.

12. The fluid delivery device according to claim 1, wherein
    in a chassis in which a first space that houses a motor forming the fluid delivery mechanism and a second space above which the reservoir is arranged are adjacent to each other, a wireless antenna that forms the sending and receiving section is arranged in the second space.

13. The fluid delivery device according to claim 12, wherein
    the wireless antenna selectively switches to one of a plurality of frequency bands to send and receive the information.

14. The fluid delivery device according to claim 12, comprising:
    a fluid injection port that is arranged in the second space and receives the fluid to be replenished in the reservoir.

15. The fluid delivery device according to claim 1, comprising:
    a connecting section that is a discharge opening for the fluid that is pressed out by the fluid delivery mechanism, wherein
    the connecting section is provided such that a path of the fluid is inclined relative to an outer circumferential surface of a chassis.

16. The fluid delivery device according to claim 15, wherein
    the connecting section is provided with an orientation such that an external elastic tube attached from the outside follows along the chassis.

17. The fluid delivery device according to claim 16, wherein
    ribs for guiding the external elastic tube are provided on the outer circumferential surface of the chassis.

18. The fluid delivery device according to claim 15, wherein
    the connecting section is provided at a linear portion of the chassis, which has an ovular shape when seen in a direction from a top surface of the reservoir.

19. The fluid delivery device according to claim 18, wherein
    the connecting section is provided within a concave portion formed in the linear portion.

20. The fluid delivery device according to claim 18, wherein
    an internal elastic tube, through which the fluid is delivered from the reservoir to the connecting section by being pressed by the fluid delivery mechanism, is arranged along an inner circumference of the ovular shape.

21. The fluid delivery device according to claim 15 wherein
the connecting section and the fluid injection port that receives the fluid to be replenished in the reservoir are arranged in a line along a replenishing direction of the fluid in the chassis.

\* \* \* \* \*